US009713574B2

(12) United States Patent
Carrel et al.

(10) Patent No.: US 9,713,574 B2
(45) Date of Patent: Jul. 25, 2017

(54) DOSE COUNTING DEVICE FOR COUPLING WITH A MEDICAL CONTAINER

(71) Applicant: Becton Dickinson France, Le Pont de Claix (FR)

(72) Inventors: Franck Carrel, Le Pont de Claix (FR); Lionel Maritan, Pierre-Chatel (FR)

(73) Assignee: Becton Dickinson France, Le Pont de Claix (FR)

( * ) Notice: Subject to any disclaimer, the term of this patent is extended or adjusted under 35 U.S.C. 154(b) by 231 days.

(21) Appl. No.: 14/418,196

(22) PCT Filed: Aug. 1, 2013

(86) PCT No.: PCT/EP2013/066160
§ 371 (c)(1),
(2) Date: Jan. 29, 2015

(87) PCT Pub. No.: WO2014/020099
PCT Pub. Date: Feb. 6, 2014

(65) Prior Publication Data

US 2015/0224028 A1 Aug. 13, 2015

(30) Foreign Application Priority Data

Aug. 3, 2012 (EP) .................................... 12305971

(51) Int. Cl.
*A61B 19/00* (2006.01)
*A61J 1/22* (2006.01)
(Continued)

(52) U.S. Cl.
CPC ............... *A61J 1/22* (2013.01); *A61J 1/1406* (2013.01); *A61J 1/1412* (2013.01); *A61J 7/04* (2013.01);
(Continued)

(58) Field of Classification Search
CPC .... A61J 1/22; A61J 1/1406; A61J 7/04; A61J 7/0436
See application file for complete search history.

(56) References Cited

U.S. PATENT DOCUMENTS 4,489,834 A 12/1984 Thackrey
4,565,302 A 1/1986 Pfeiffer et al.
(Continued)

FOREIGN PATENT DOCUMENTS

EP 0114617 A2 8/1984
EP 0836465 A1 4/1998
(Continued)

*Primary Examiner* — Leslie Deak
(74) *Attorney, Agent, or Firm* — The Webb Law Firm

(57) ABSTRACT

The present invention relates to a dose counting device (10) for coupling with a medical container filled with a number N of doses of a product to be withdrawn therefrom, said medical container being provided with an opening for access to said product, the dose counting device comprising: —a gripping member (20) for securing the dose counting device to the medical container, said gripping member including a hole (44) intended to face said opening when said dose counting device is coupled to said medical container, —a counting ring (30) rotatably mounted with respect to said gripping member, said counting ring being provided with information data corresponding to the N doses, a cover (50) movable with respect to said opening between a closed position, in which said cover prevents access to said opening and to said product, and an open position, in which it does not prevent access to said opening and product.

15 Claims, 10 Drawing Sheets

Figure 1A:
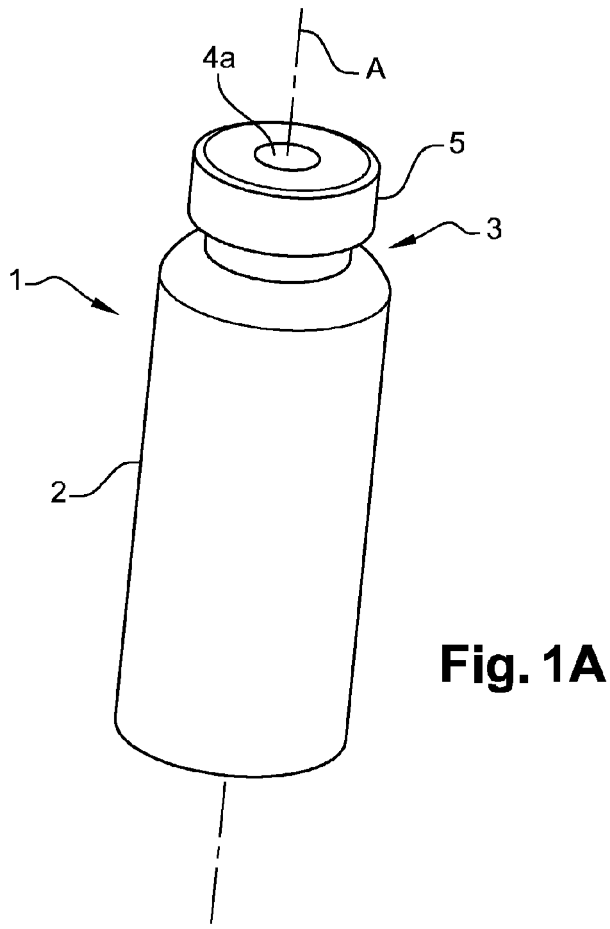

(51) Int. Cl.
*A61J 1/14* (2006.01)
*A61J 7/04* (2006.01)

(52) U.S. Cl.
CPC ..... *A61J 7/0436* (2015.05); *F04C 2270/0421* (2013.01)

(56) References Cited

U.S. PATENT DOCUMENTS

| | | | | |
|---|---|---|---|---|
| 4,705,182 | A | 11/1987 | Newel-Lewis | |
| 4,782,966 | A | 11/1988 | Thackrey | |
| 5,498,253 | A | 3/1996 | Aswad et al. | |
| 5,620,433 | A | 4/1997 | Aswad et al. | |
| 5,678,718 | A | 10/1997 | Morris et al. | |
| 5,765,706 | A * | 6/1998 | Barker | A61J 7/04 116/309 |
| 5,803,284 | A | 9/1998 | Grimard | |
| 6,453,956 | B2 | 9/2002 | Safabash | |
| 6,880,722 | B2 | 4/2005 | Anderson et al. | |
| 7,100,646 | B2 | 9/2006 | Py et al. | |
| 7,263,411 | B2 | 8/2007 | Shows et al. | |
| 7,382,692 | B1 | 6/2008 | Hildebrandt | |
| 7,464,708 | B2 | 12/2008 | Marx | |
| 7,530,974 | B2 | 5/2009 | Domkowski et al. | |
| 7,621,273 | B2 | 11/2009 | Morton et al. | |
| 7,648,491 | B2 | 1/2010 | Rogers | |
| 7,805,216 | B2 | 9/2010 | Shows et al. | |
| 7,819,285 | B2 | 10/2010 | Mochizuki et al. | |
| 8,002,130 | B2 | 8/2011 | Thilly | |
| 8,034,042 | B2 | 10/2011 | Domkowski et al. | |
| 8,090,471 | B2 | 1/2012 | Shows et al. | |
| 8,091,727 | B2 | 1/2012 | Domkowski | |
| 8,113,199 | B2 | 2/2012 | Augustyn et al. | |
| 8,122,923 | B2 | 2/2012 | Kraus et al. | |
| 8,225,949 | B2 | 7/2012 | Aneas | |
| 8,303,572 | B2 | 11/2012 | Adair et al. | |
| 8,479,732 | B2 | 7/2013 | Stuart et al. | |
| 2007/0108205 | A1 | 5/2007 | Porras | |
| 2007/0246042 | A1 | 10/2007 | Purkins et al. | |
| 2009/0050213 | A1 | 2/2009 | Biddell et al. | |
| 2009/0314291 | A1 | 12/2009 | Anderson et al. | |
| 2010/0004619 | A1 * | 1/2010 | Rondeau | F16L 37/0985 604/407 |
| 2010/0059474 | A1 | 3/2010 | Brandenburger et al. | |
| 2011/0074148 | A1 | 3/2011 | Imai | |
| 2011/0144614 | A1 | 6/2011 | Hereford | |
| 2011/0266249 | A1 | 11/2011 | Kakutani et al. | |
| 2012/0000569 | A1 | 1/2012 | Wiegel | |
| 2012/0116579 | A1 | 5/2012 | Shows et al. | |
| 2012/0123381 | A1 | 5/2012 | Kraus et al. | |
| 2012/0203193 | A1 | 8/2012 | Rogers | |
| 2012/0223045 | A1 | 9/2012 | Burke, Jr. | |
| 2013/0197467 | A1 | 8/2013 | Schuetz et al. | |
| 2013/0204201 | A1 | 8/2013 | Avery et al. | |
| 2013/0253432 | A1 | 9/2013 | Avery et al. | |
| 2014/0163468 | A1 | 6/2014 | Avery et al. | |

FOREIGN PATENT DOCUMENTS

| | | | |
|---|---|---|---|
| EP | 1034772 | A1 | 9/2000 |
| EP | 2555814 | A1 | 2/2013 |
| EP | 2555815 | A1 | 2/2013 |
| EP | 2603260 | A1 | 6/2013 |
| GB | 2179778 | A | 3/1987 |
| JP | 10118155 | A | 5/1998 |
| WO | 9640037 | A1 | 12/1996 |
| WO | 2004073775 | A1 | 9/2004 |
| WO | 2006016726 | A1 | 2/2006 |
| WO | 2011124631 | A1 | 10/2011 |
| WO | 2011124632 | A1 | 10/2011 |
| WO | 2012020083 | A1 | 2/2012 |

* cited by examiner

DOSE COUNTING DEVICE FOR COUPLING WITH A MEDICAL CONTAINER

CROSS REFERENCE TO RELATED APPLICATIONS

This application is the United States national phase of International Application No. PCT/EP2013/066160 filed Aug. 1, 2013, and claims priority to European Patent Application No. 12305971.9 filed Aug. 3, 2012, the disclosures of which are hereby incorporated in their entirety by reference.

The present invention relates to a dose counting device for coupling to a medical container filled with a certain number of doses of a product, such as a vial containing a pharmaceutical product, such as a vaccine, said dose counting device allowing for counting the doses withdrawn from the medical container in an aseptic manner.

In this application, the distal end of a component or apparatus must be understood as meaning the end furthest from the hand of the user and the proximal end must be understood as meaning the end closest to the hand of the user, with reference to the injection device intended to be used with said component or apparatus. As such, in this application, the distal direction must be understood as the direction of injection with reference to the injection device, and the proximal direction is the opposite direction, i.e. the direction of the transfer of the product from the vial to the injection device.

One of the ways to improve health is to immunize entire populations against a number of diseases. To date, injection administration is the most common method of administering vaccines.

Each year, numerous drugs, for example vaccines, need to be prepared throughout the world by healthcare institutions. Many vaccine compositions are usually not stable at room temperature and they must be stored at rather specific cold temperatures. Indeed, due to their biological nature, vaccines are complex to handle and to store. Vaccines are usually temperature sensitive and typically need to be maintained and stored at all time between 2 and 8 degrees Celsius (° C.). Some vaccines will be more sensitive to heat exposure and others will be sensitive to freezing. Therefore, maintaining and monitoring the appropriate temperatures during the storage and the handling of vaccines is a critical issue in order to sustain their efficacy. Overexposure to heat as well as overcooling may result in the destruction of the biological elements of the vaccines. Use of vaccines not stored in appropriate conditions may lead to not effective vaccination of the populations against diseases and would lead to expensive campaigns with limited results.

Furthermore, it is critical that the cold chain be not interrupted from production of the drug at a pharmaceutical company to its administration to the patient.

From a supply chain perspective, the most efficient vaccine packaging is the multidose container such as multidose vial, that is to say, vial that may contain up to 10, 100 or 1000 doses of vaccine, one dose being intended for one patient. These vials are usually closed by a septum. In preparation of an injection of a vaccine, the user pierces the septum of the vial with the needle of an empty syringe, he then fills the syringe with one dose of vaccine and proceeds to the injection of the vaccine to the patient.

As such, multidose vials imply that the septum of the vial be pierced successively a high number of times, namely as many as the number of doses present in the vial. In order to ensure safe injections, the sterility of the septum of the vial should be maintained during the whole time the vial is used.

Anyway, in locations where it is difficult to maintain good hygienic conditions such as remote locations which are far from towns and from hospital facilities, the multidose vials may be handled and manipulated at ambiant air. In such cases, the septum of the vial may be contaminated either by the ambiant air, or, each time a dose of vaccine is removed, by the needle of the empty syringe used.

In addition, in regions where there is limited or potentially no supply of energy to power cooling equipment such as a refrigerator, the multidose vials may be maintained in cold conditions by simple contact with ice packs. As time goes by, part of the ice may melt and turn into water, and the septum of the multidose vials may be in contact with such water that may contaminate the septum of the vial.

It may then happen that a multidose vial, such as for example a 10-dose vial, is opened and that only three doses are used, for vaccinating three patients only, the remaining content of the vial being wasted because not intended to be administered in a sufficiently short time after opening of the vial in order to guaranty the vaccine or drug sterility.

Vaccination campaigns can therefore be made difficult in some regions and a significant proportion of vaccines may be wasted by the time they reach their target. This has an unacceptable cost to the health organizations in charge of immunization campaigns. In addition, it may happen that in case of vaccination campaigns, or pandemic, hundreds of patients need to be vaccinated in a very short time, in locations where it is difficult to maintain good hygienic conditions such as remote locations which are far from towns and from hospital facilities.

Therefore, it would be desirable to provide a device that would allow several successive piercings of a multidose vial septum and that would guarranty that said piercings be carried out in aseptic conditions, in particular that the septum be maintained sterile during the lifetime of the multidose vial, and that would allow to precisely count the number of doses of product already withdrawn from the vial or on the contrary still remaining in the vial.

Moreover there is a need to provide a device that enhances the supply chain of drugs and vaccines and that prevents wastage of valuable medicine during immunization campaigns.

In addition, there is a need for a dose counting device usable with a medical container, that would provide reliable information to the user regarding the number of doses of product already withdrawn from, or still remaining within, the container, even if the user happens to accidentally start to open the medical device before changing his mind and closing it.

A first aspect of the present invention is a dose counting device for coupling with a medical container filled with a number N of doses of a product to be withdrawn therefrom, said medical container being provided with an opening for access to said product, the dose counting device comprising:

a gripping member for securing the dose counting device to the medical container, said gripping member including a hole intended to face said opening when said dose counting device is coupled to said medical container, a counting ring rotatably mounted with respect to said gripping member, said counting ring being provided with information data corresponding to the N doses, a cover movable with respect to said hole between a closed position, in which said cover prevents access to said hole, and an open position, in which it does not prevent access to said hole.

The dose counting device of the invention is intended to be mounted on and coupled with a medical container, such as for example a conventional vial for storing pharmaceutical products, such as multidose vials for vaccines. Such a vial 1 is shown on FIGS. 1A-1C and generally comprises a tubular barrel 2 having a longitudinal axis A, closed at an end and having a collar 3 at the opposite end, said collar 3 forming an opening 3*a* closed by a septum 4. Usually, the septum 4 is fixedly attached to the collar 3 of the vial 1 by a peripheral band 5, said peripheral band 5 leaving a part of the septum 4, herein called outer surface 4*a* of the septum, directly facing the outside of the vial 1, namely the outside environment. The septum 4 is usually made of a material impermeable to gas and liquid and it seals hermetically the content of the vial 1. The septum 4 is also pierceable by the needle of an injection device intended to be filled with the product contained in the vial, said septum 4 being accessible to said needle via its outer surface 4*a*.

Alternatively, the dose counting device could be used in combination with a medical container that has an opening not closed by a septum.

Figure 1B:
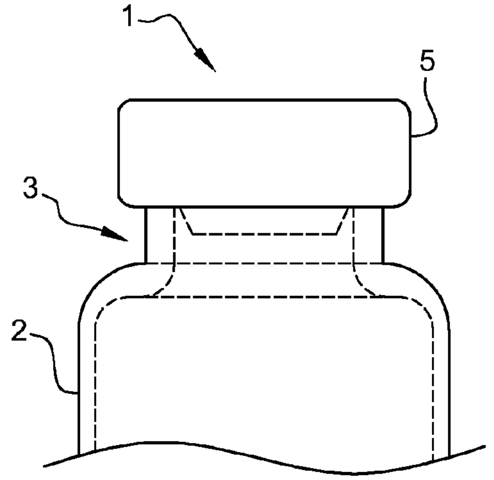
Figure 1C:
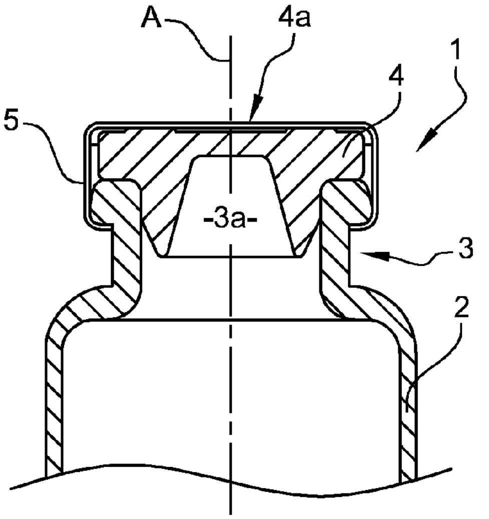

Although the following description describes the use of the dose counting device of the invention with a vial closed by a septum as shown on FIGS. 1A-1C, the dose counting device of the invention could be used in combination with, and mounted on, a medical container free of any septum. For example, the medical container may be a bottle, an ampoule, a flask or any other container usable in the medical field as long as it is provided with an opening for accessing the product it contains, regardless from the fact that this opening is closed or not by a septum.

The dose counting device of the invention allows the user to be informed of how many doses of product are left in the medical container, for example a vial, while maintaining good hygienic conditions during the withdrawal of doses of product from the medical container, for example a vial. Indeed, the dose counting device of the invention allows protecting the opening of the medical container, for example a vial, during the whole lifetime of the medical container, for example a vial, namely during the successive withdrawals of the N number of doses of product initially present in the medical container, for example a vial. The good hygienic conditions of the medical container are therefore maintained.

The gripping member of the dose counting device of the invention may be any member capable of securing the dose counting device on the medical container, and in particular around the collar of the medical container, either in a temporary or permanent way. The connection of the gripping member to the medical container may be a lateral or an axial connection.

In embodiments, the dose counting device further comprises an incrementing system coupled to said cover and to said counting ring, said incrementing system allowing the counting ring to automatically rotate on a predetermined angle, each time said cover moves from its closed position to its open position and back to its closed position. In particular, in embodiments, the dose counting device further comprises an incrementing system coupled to said cover and to said counting ring, said incrementing system allowing the counting ring to automatically rotate on a predetermined angle, each time said cover moves from its open position to its closed position. The user therefore needs not rotating manually the counting ring, as said counting ring is automatically incremented each time the user moves the cover from its closed position to its open position, and back to its closed position, and preferentially each time the user moves the cover from its open position to its closed position. In such embodiments, the dose counting device is therefore a passive device, as the user just has to open the cover and close it again, the cover itself completing the increment of the dose counting. The counting is done by the handling of the cover.

In embodiments, said incrementing system comprises an active surface and said counting ring comprises a complementary active surface, said active surface engaging and cooperating with said complementary active surface so as to rotate said counting ring, when said cover moves back from its open position to its closed position.

The rotation of the counting ring, which is provided with information data corresponding to the N doses, is therefore dependent on a two-step process, namely moving the cover from its closed position to its open position in a first step, and moving the cover from its open position to its closed position in a second step, the rotation of the counting ring taking place only during the second step. This system therefore tolerates incomplete or accidental manipulation of the cover by the user while preserving the reliability of the information data corresponding to the N doses which may be displayed to the user. Indeed, since the counting ring rotates only during the second step, if the user, accidentally or not, performs the first step only partially, then the rotation of the counting ring will not take place and the information data corresponding to the N doses provided on the counting ring will not change. The user is therefore provided with accurate information on the counting ring and risks of confusion are eliminated.

In embodiments, said cover being movable in rotation around an axis R with respect to said gripping member when said cover moves from its closed position to its open position and vice-versa, said incrementing system comprises a part of a gear wheel located on said cover, said gear wheel being rotatable around axis R and being provided with a plurality of radial teeth capable of cooperating with a plurality of complementary radial teeth provided on the periphery of the counting ring, when said cover moves back from its open position to its closed position.

Alternatively, said cover being movable in translation with respect to said gripping member, when said cover moves from its closed position to its open position and vice-versa, said incrementing system comprises a flexible leg located on said cover, said flexible leg being capable of escaping a sloped surface of the periphery of said counting ring when said cover moves from its closed position to its open position, said flexible leg engaging a radial surface of said periphery of said counting ring when said cover moves back from its open position to its closed position. Said flexible leg therefore causes movement, namely rotation, of the counting ring during the second step of the process when the cover moves from its open position to its closed position.

Alternatively, in other embodiments, said cover being movable in translation with respect to said gripping member, when said cover moves from its closed position to its open position and vice-versa, said incrementing system comprises a flexible leg located on said cover, said flexible leg being capable of engaging a radial surface of said periphery of said counting ring when said cover moves from its closed position to its open position, thereby causing rotation of the counting ring.

In embodiments, the dose counting device further comprises a pierceable elastomeric piece fixed with respect to the gripping member and intended to face the opening of the medical container when said dose counting device is coupled to said medical container, regardless from the position of the cover. In embodiments, the pierceable elastomeric piece is lodged within the hole of the gripping member of the dose counting device.

In the present application, "pierceable" means that the septum and the elastomeric piece may be pierced and traversed by the needle of an injection device such as a syringe, an auto-injector, or a reconstitution device, in order to reach the opening of the vial and withdraw a dose of product therefrom.

In embodiments, the elastomeric piece is made of a gas and liquid impermeable material capable of flexing under pressure. For example, the elastomeric piece has a thickness ranging from 1 to 8 mm, preferably from 2 to 4 mm. The elastomeric piece may show a hardness ranging from 10 to 100 Shore A, preferably from 40 to 70 Shore A, measured according to standard DIN 53505.

Suitable materials for the pierceable elastomeric piece of the adaptor of the invention include natural rubber, acrylate-butadiene rubber, cis-polybutadiene, chloro or bromobutyl rubber, chlorinated polyethylene elastomers, polyalkylene oxide polymers, ethylene vinyl acetate, fluorosilicone rubbers, hexafluoropropylene-vinylidene fluoride-tetrafluoroethylene terpolymers, butyl rubbers, polyisobutene, synthetic polyisoprene rubber, silicone rubbers, styrene-butadiene rubbers, tetrafluoroethylene propylene copolymers, thermoplastic-copolyesters, thermo-plastic elastomers, or the like or a combination thereof.

In embodiments, the pierceable elastomeric piece is self-resealing. "Self-resealing" means in the present application that the elastomeric piece closes automatically and rapidly the hole produced by the piercing of the needle, for example in less than 0.5 seconds, once the needle is removed from the elastomeric piece. This automatic closure step may occur a high number of times, for example as many times as necessary for removing the N doses of products contained in the multidose medical container. This automatic obstruction restricts or prevents air and/or contaminants from entering inside the medical container, but also at the interface between the elastomeric piece and the septum, and thus allows asepsis maintenance. Moreover, the presence of the pierceable elastomeric piece gives time to the septum of the medical container to reseal, as the needle is still present in the pierceable elastomeric piece after it is removed from the septum. As such, neither air nor contaminants may be introduced in the medical container, or at the interface between the elastomeric piece and the septum, even if the medical container is maintained under negative pressure after the withdrawal of one or more doses of product. In addition, the septum of the medical container may itself be self-resealing.

Suitable materials for self-resealing pierceable elastomeric piece include synthetic polyisoprene, natural rubber, silicone rubber, thermo-plastic elastomers, or the like or a combination thereof.

The dose counting device of the invention therefore allows access to, and for example by piercing the septum of, the medical container in good hygienic conditions multiple successive times. Indeed, when the user decides to fill in an empty syringe with a dose of drug contained in the medical container, he simply secures the dose counting device of the invention on the medical container by means of the gripping member. Once the dose counting device is secured on the medical container, the hole of the dose counting device faces the opening of the medical container, and the pierceable elastomeric piece, if present within said hole, is in contact with the outer surface of the septum, if present, of the medical container. Then, the user just has to open the cover of the dose counting device which protects the septum and/or the pierceable elastomeric piece. As a consequence, introducing the needle in the medical container implies that the needle pierces and traverses the elastomeric piece in the first place. During this step, the needle mechanically rubs against the material forming the elastomeric piece and it is naturally cleaned, as the potential bacteria are wiped out from the needle when said needle penetrates the elastomeric piece. In addition, once the needle protrudes out of the elastomeric piece, it directly enters the septum of the medical container and may therefore not be contaminated by foreign elements.

The user may repeat the piercing step with the needle of a new empty injection device until all the doses contained in the medical container are removed. The dose counting device of the invention acts as a protection of the septum.

In embodiments, the dose counting device further comprises biasing means for forcing the cover in its closed position. The biasing means ensures that the dose counting device is not left in the open position of the cover for an extended period of time and therefore reduces the risk of contamination of the pierceable elastomeric piece and/or the septum of the medical container.

Another aspect of the invention is an assembly comprising a medical container comprising an opening and filled with a number N of doses of a product to be withdrawn therefrom via said opening and a dose counting device as described above. Said opening may be closed by a septum. In embodiments, when said dose counting device is coupled to said medical container, said pierceable elastomeric piece is in contact with said septum.

As such, whatever the piercing location of the pierceable elastomeric piece by the needle, the user is ensured that the distal tip of the needle will directly pierce the septum after being passed through the pierceable elastomeric piece. Therefore, said distal tip is not in contact with ambient air or with other elements that would be trapped between the outer surface of the septum and the surface of the pierceable elastomeric piece. In particular, in such embodiments, the outer surface of the septum and the surface of the pierceable elastomeric piece match each other in such a way that they are in intimate contact together on their entire surface and lead to a closed interface.

The septum is therefore protected by the pierceable elastomeric piece. Risks of contaminating the septum by the needle are therefore decreased. In embodiments, said opening being a collar closed by a septum, said gripping member comprises a clip capable of substantially surrounding said collar. The dose counting device is therefore well secured on the vial.

Figure 2:
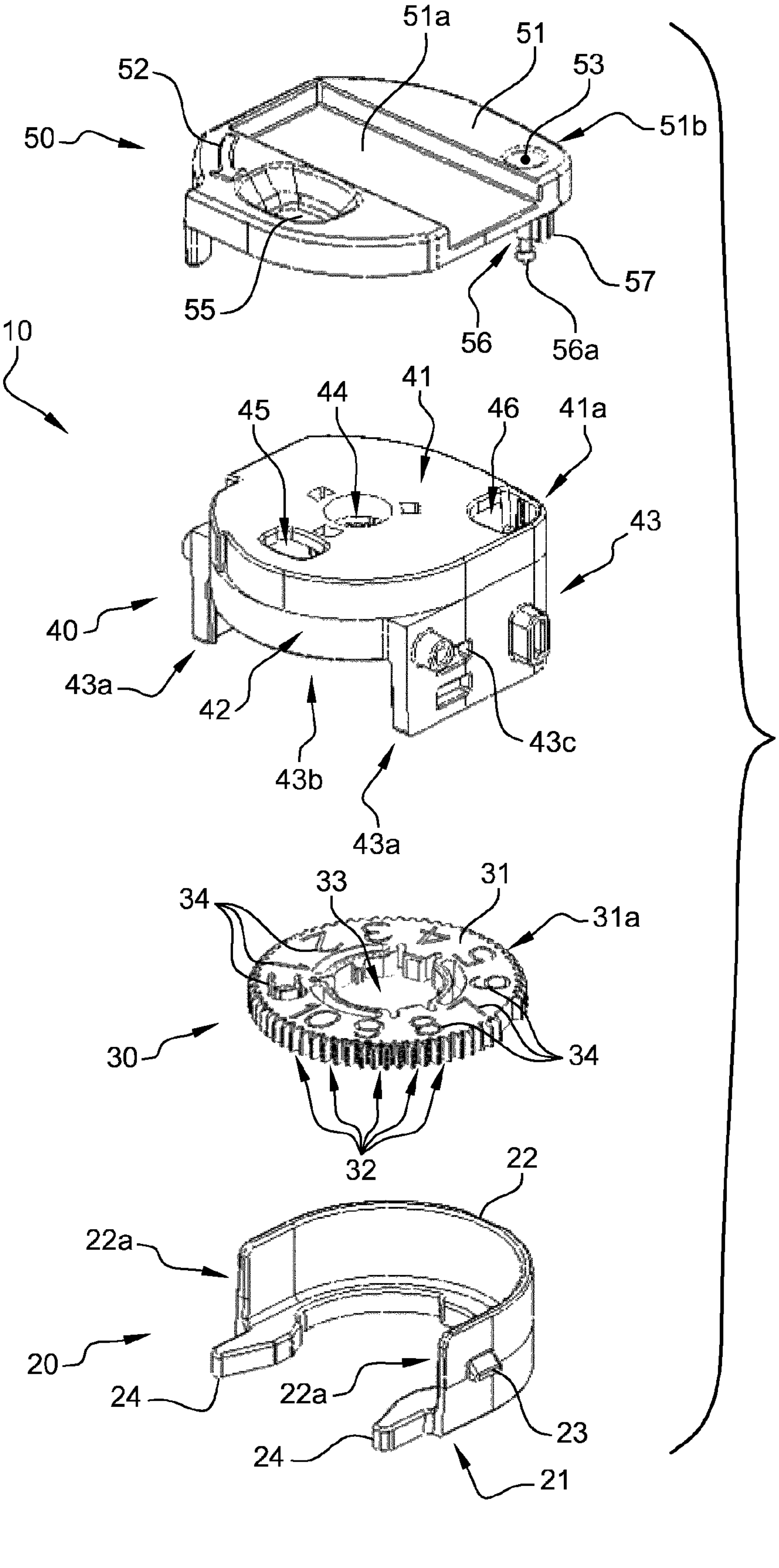
Figure 3:
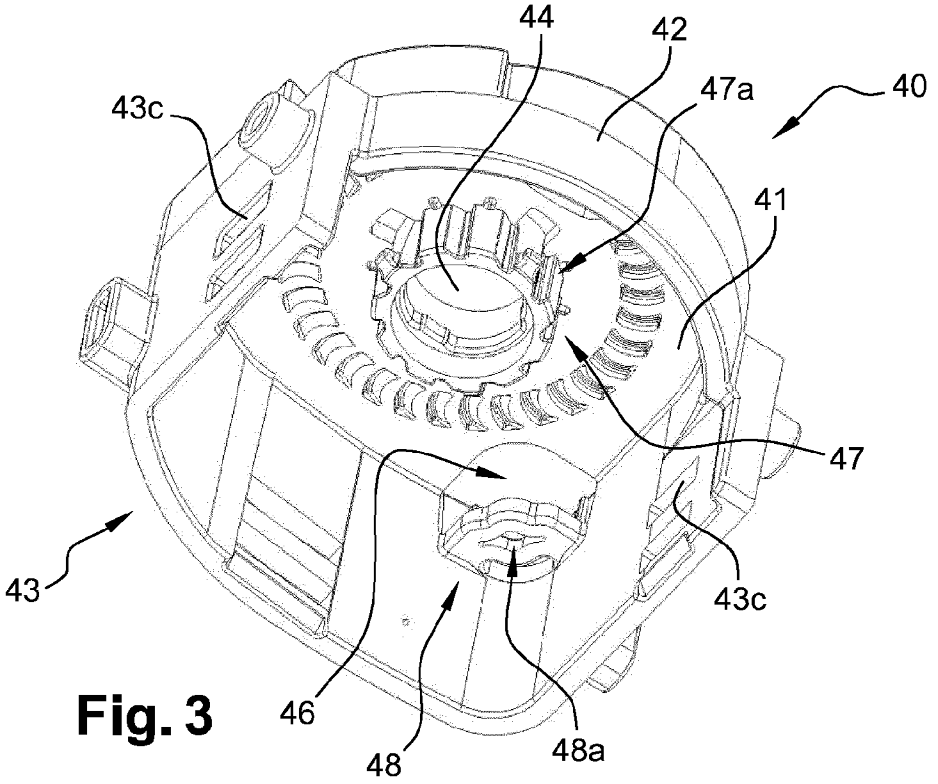
Figure 4:
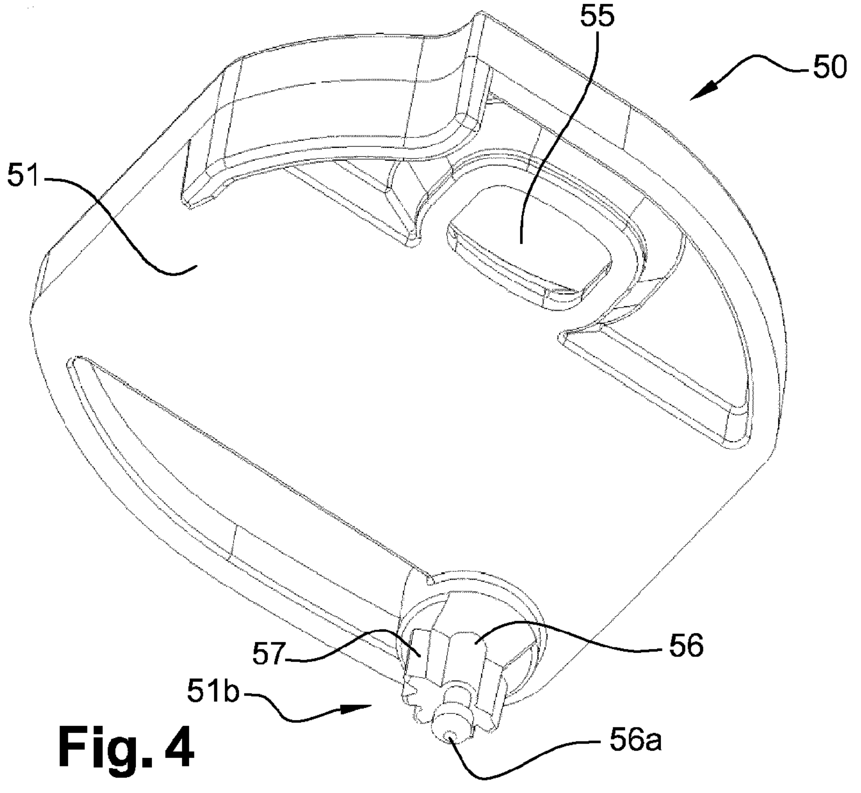
Figure 5A:
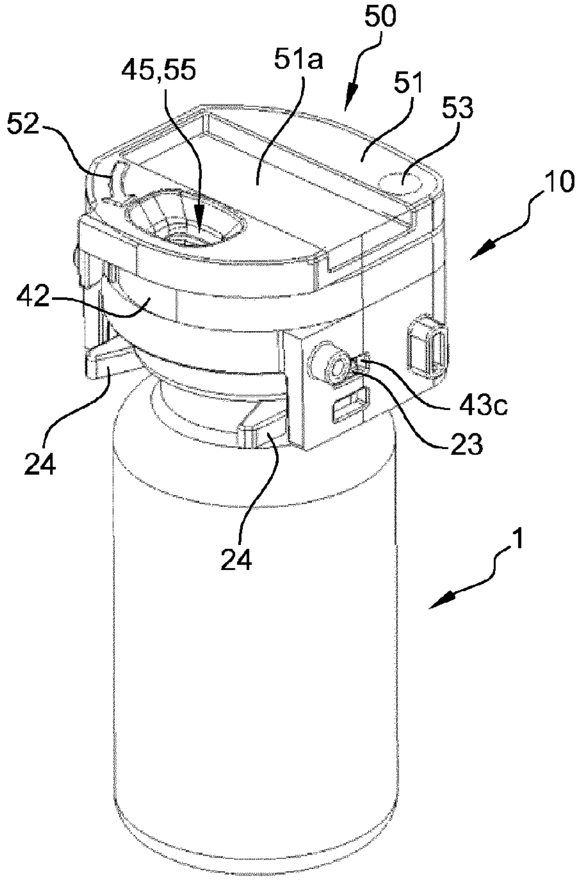
Figure 5B:
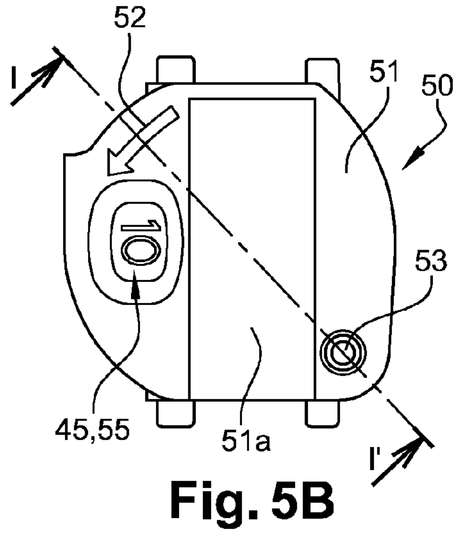
Figure 5C:
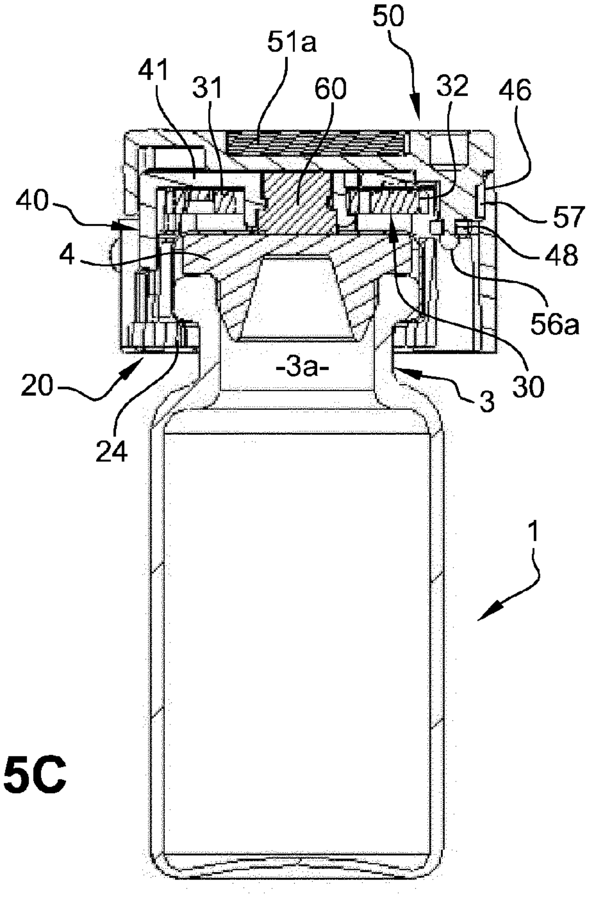
Figure 6A:
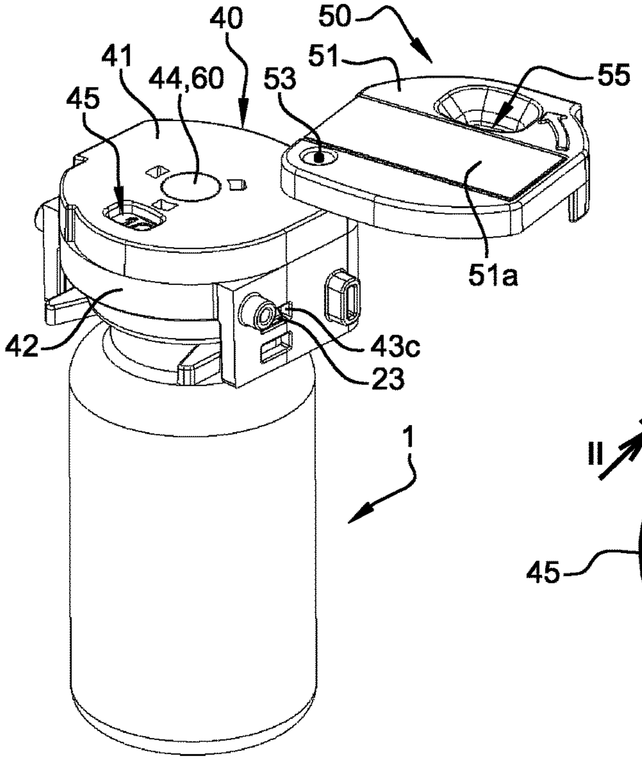
Figure 6B:
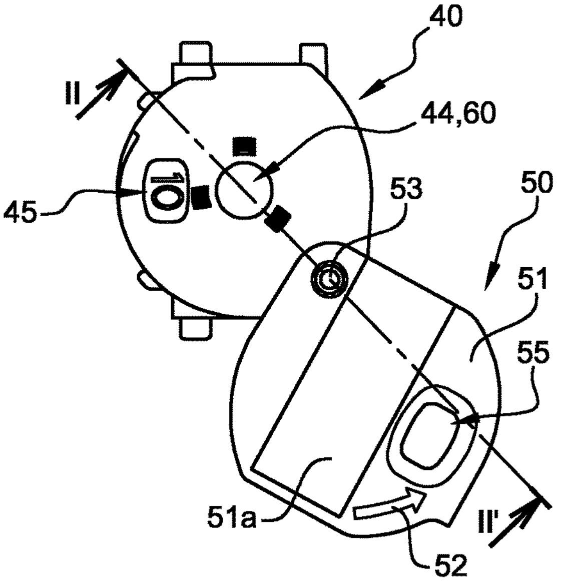
Figure 6C:
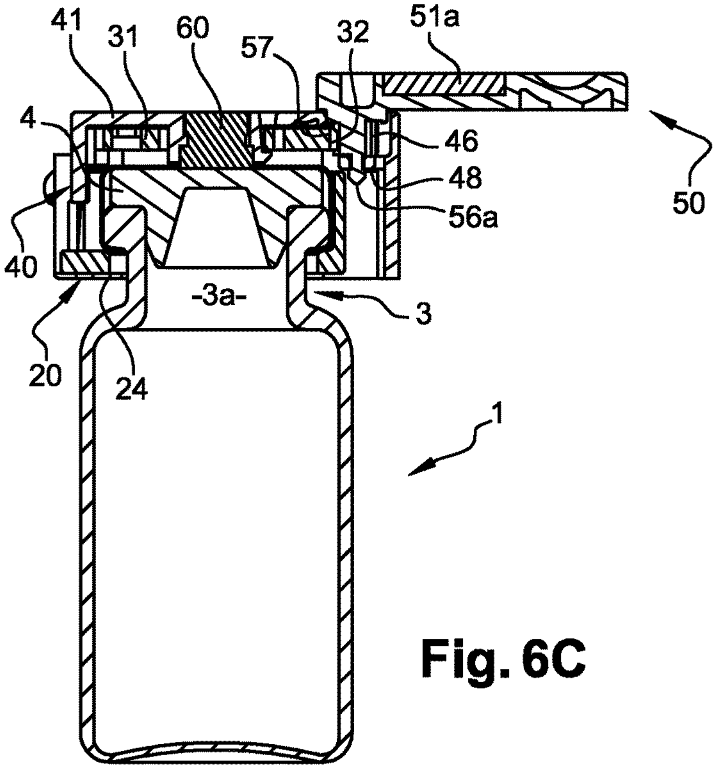
Figure 7:
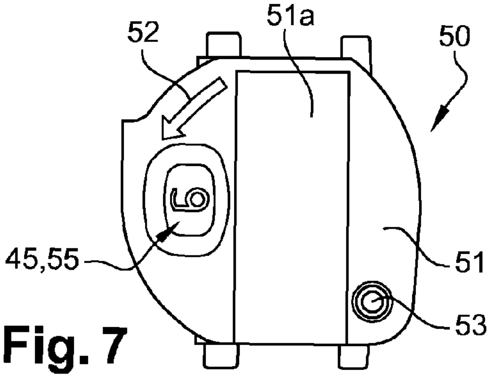
Figure 8:
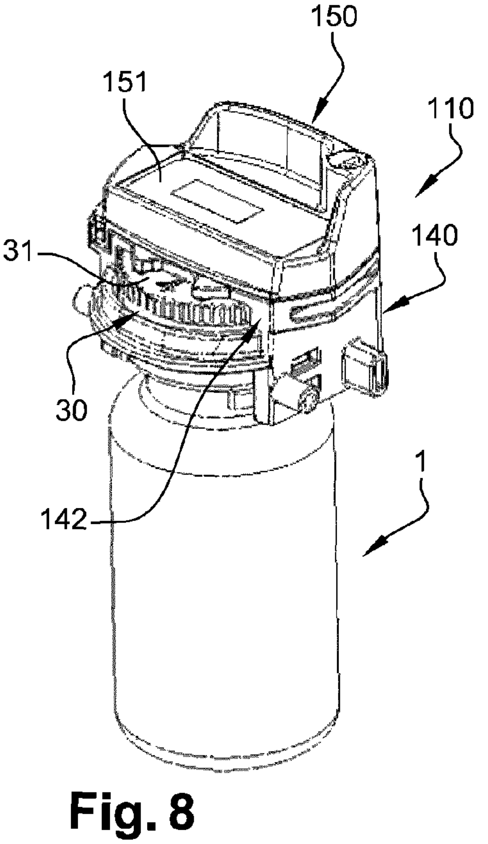
Figure 9:
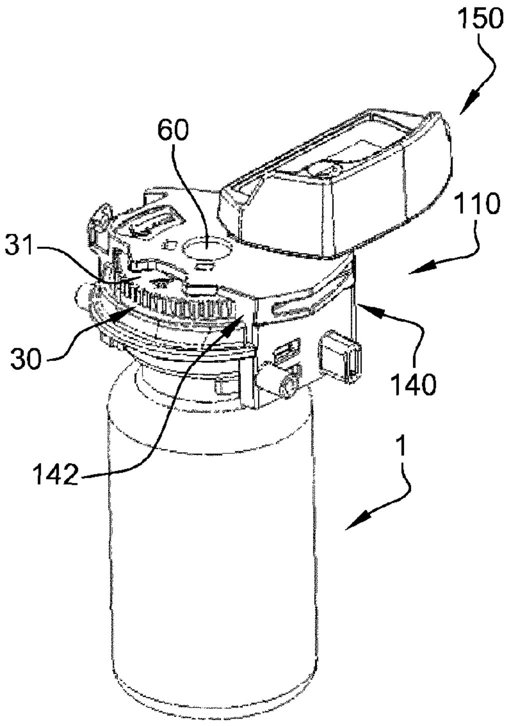
Figure 10:
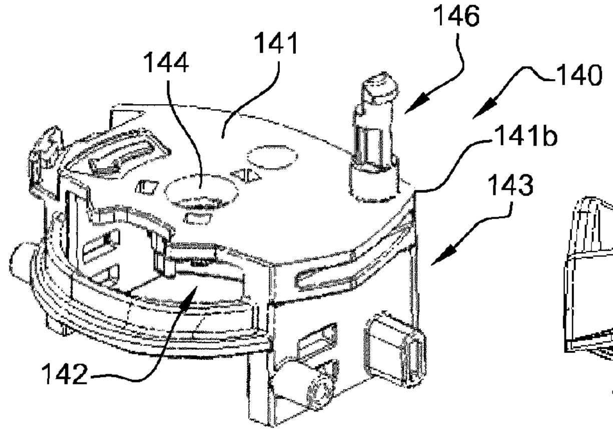
Figure 11:
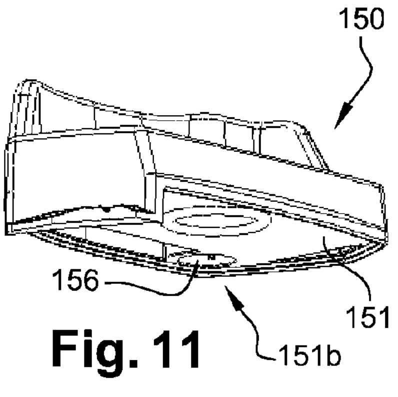
Figure 12:
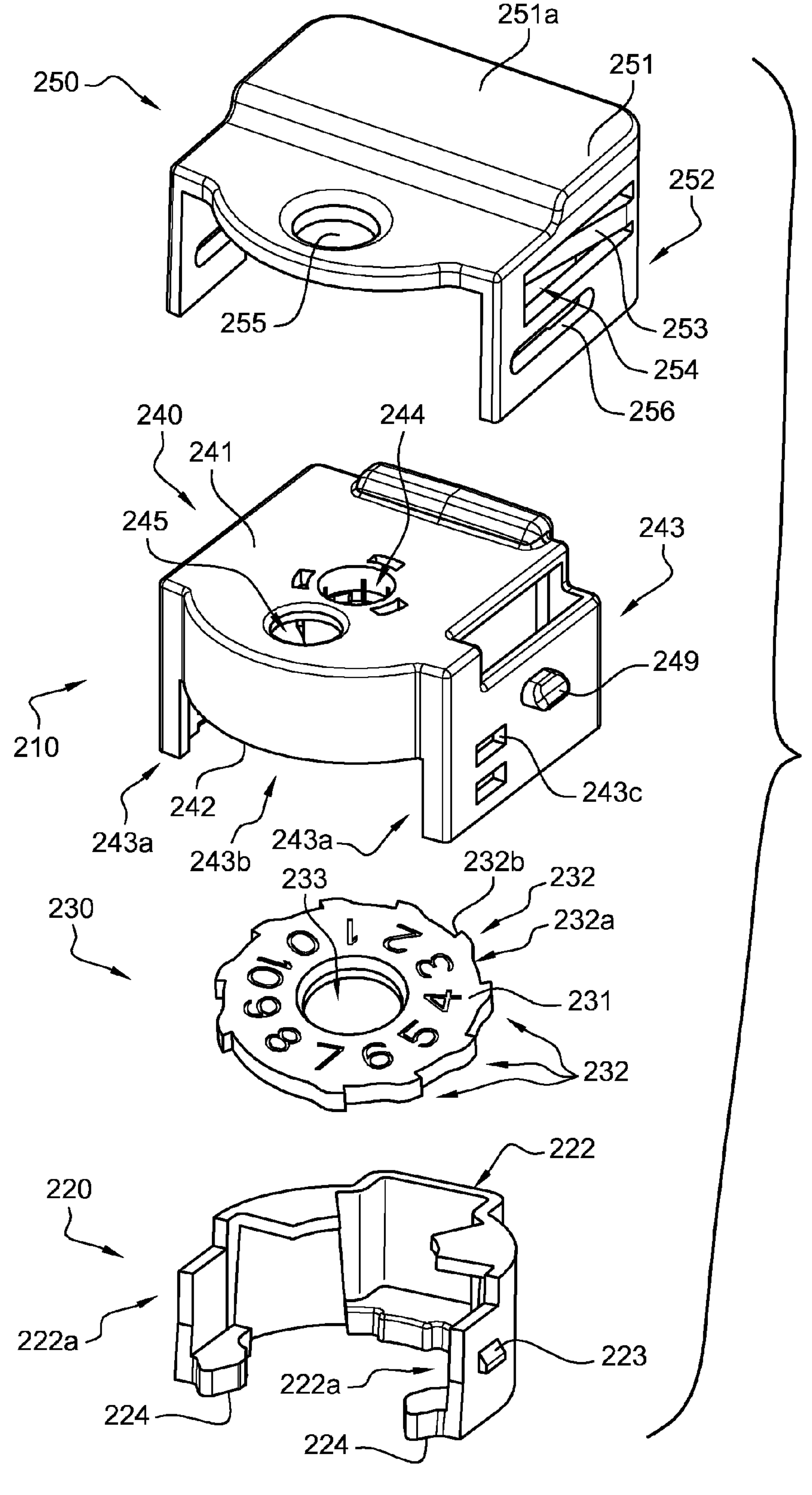
Figure 13:
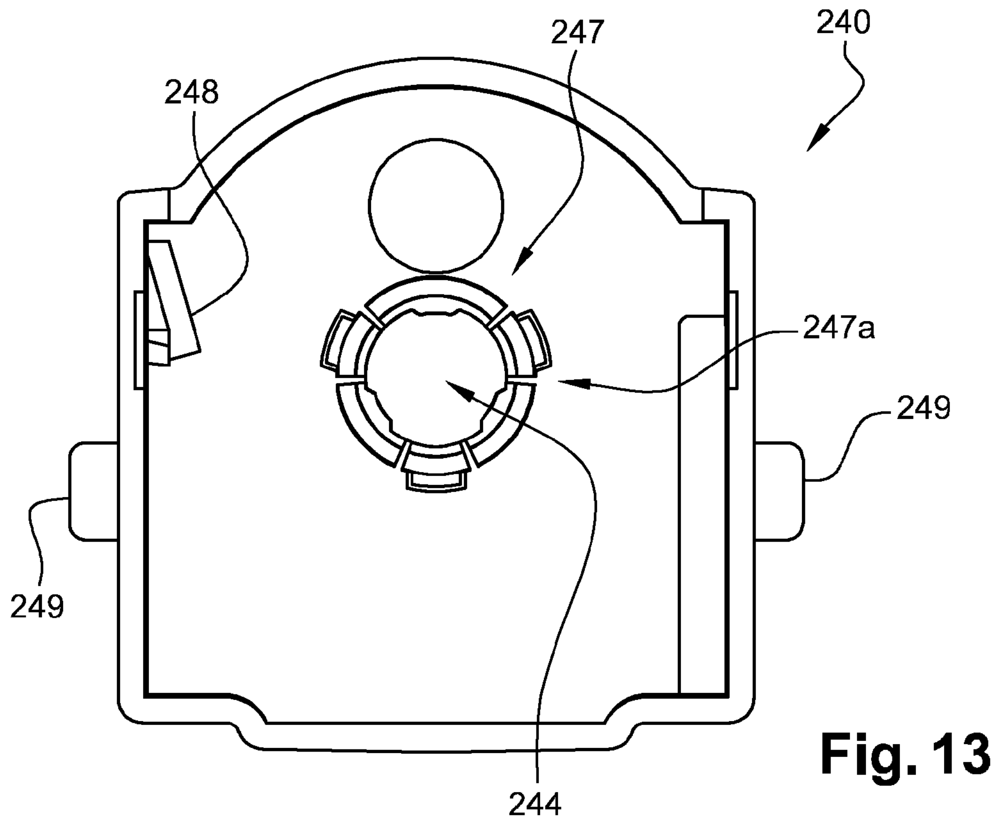
Figure 14:
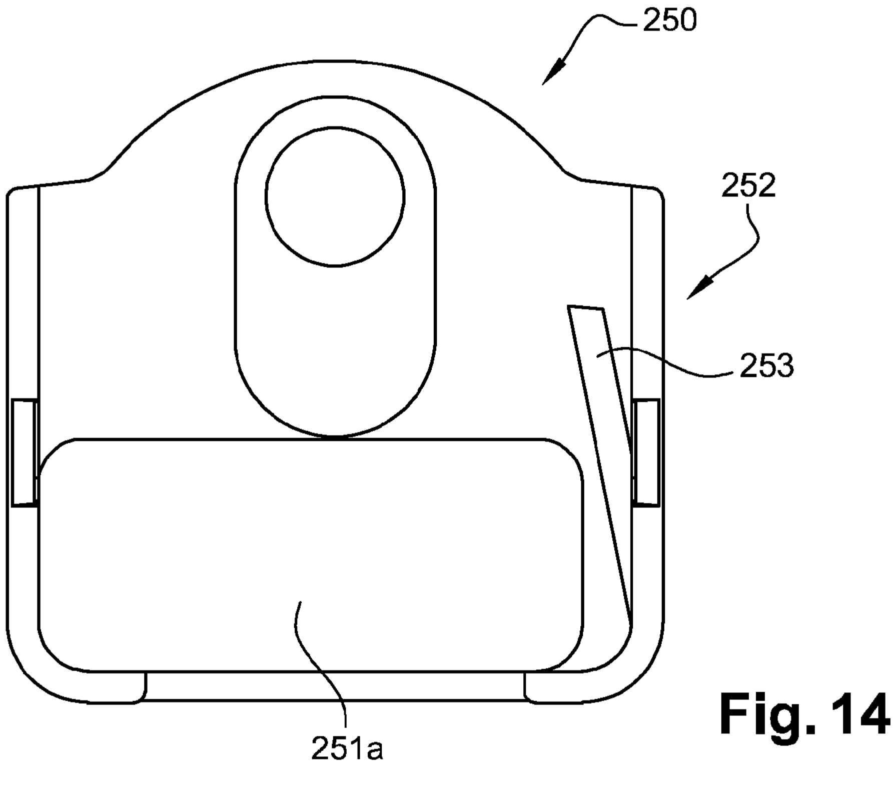
Figure 15A:
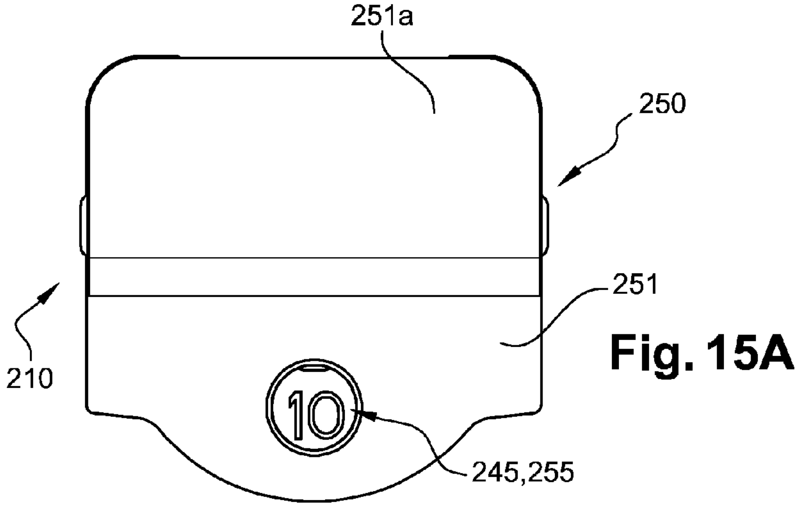
Figure 15B:
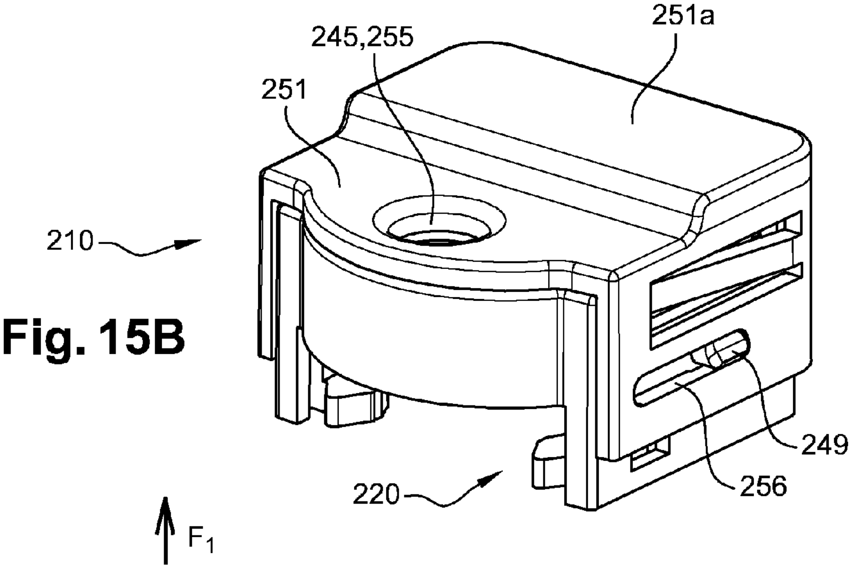
Figure 15C:
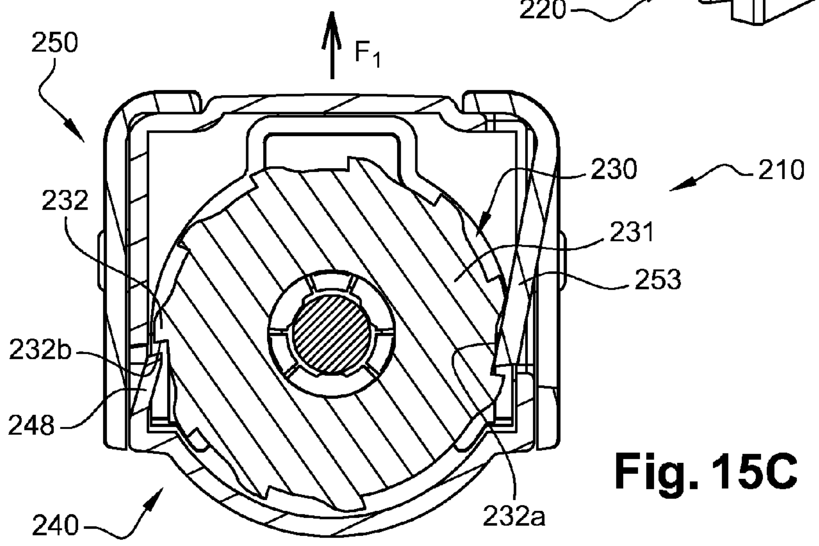
Figure 16A:
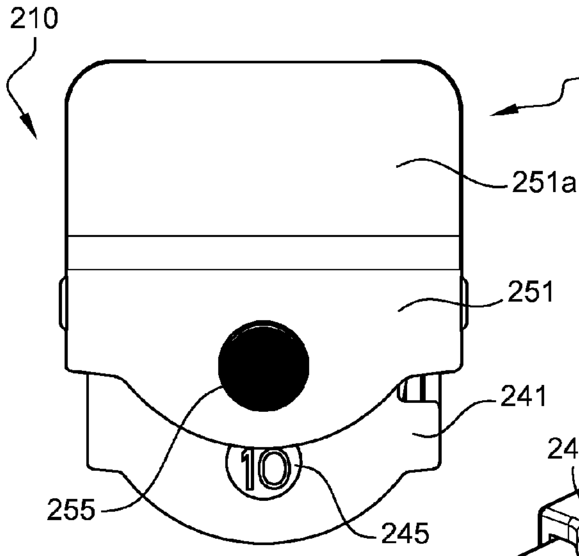
Figure 16B:
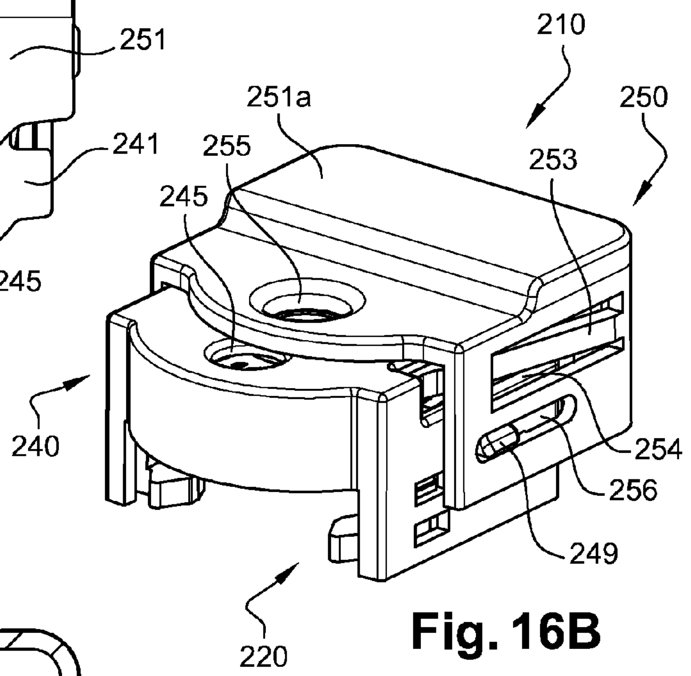
Figure 16C:
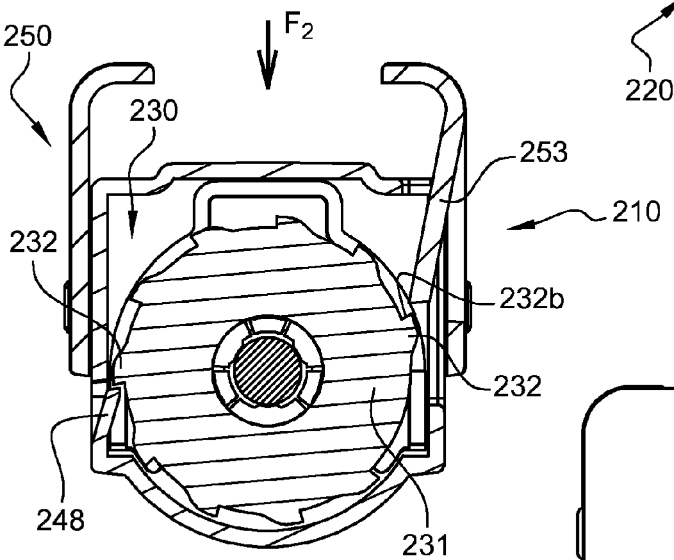
Figure 17:
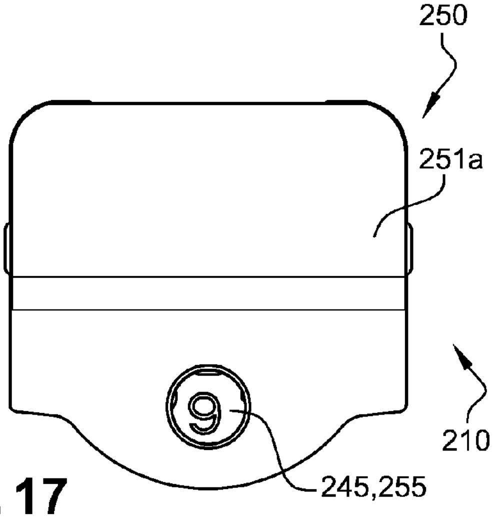

The present invention will now be described in greater detail based on the following description and the appended drawings in which:

FIGS. 1A-1C are respectively a perspective view, a partial side view and a partial cross section view of a conventional vial on which the dose counting device of the invention is to be mounted, FIG. 2 is an exploded perspective view of a first embodiment of the dose counting device of the invention, FIG. 3 is a perspective view from the bottom of a part of the gripping member of the dose counting device of FIG. 2, FIG. 4 is a perspective view from the bottom of the cover of the dose counting device of FIG. 2, FIGS. 5A-5C are respectively a perspective view, a top view and a cross section view along line I-I' of FIG. 5B, of the dose counting device of FIG. 2 once mounted on the vial of FIGS. 1A-1C, in the closed position of the cover, FIGS. 6A-6C are respectively a perspective view, a top view and a cross section view along line II-II' of FIG. 6B, of the dose counting device of FIG. 2 once mounted on the vial of FIGS. 1A-1C, in the open position of the cover, FIG. 7 is a top view of the dose counting device of FIGS. 6A-6C, once the cover has moved back to its closed position, FIG. 8 is a perspective view of a second embodiment of the dose counting device of the invention, mounted on the vial of FIGS. 1A-1C, in the closed position of the cover, FIG. 9 is a perspective view the dose counting device of FIG. 8, in the open position of the cover, FIG. 10 is a perspective view of a part of the gripping member of the dose counting device of FIGS. 8-9, FIG. 11 is a perspective view of the cover of the dose counting device of FIGS. 8-9, FIG. 12 is an exploded perspective view of a third embodiment of the dose counting device of the invention, FIG. 13 is a bottom view of a part of the gripping member of the dose counting device of FIG. 12, FIG. 14 is a bottom view from of the cover of the dose counting device of FIG. 12, FIGS. 15A-15C are respectively a top view, a perspective view, and a bottom view of the dose counting device of FIG. 12, in the closed position of the cover, FIGS. 16A-16C are respectively a top view, a perspective view, and a bottom view of the dose counting device of FIG. 12, in the open position of the cover, FIG. 17 is a top view of the dose counting device of FIGS. 16A-16C, once the cover has moved back to its closed position.

With reference to FIG. 2 is shown an exploded view of a dose counting device 10 in accordance with a first embodiment of the invention, intended to be coupled on a multidose vial 1 as shown on FIGS. 1A-1C.

As mentioned above, although the following description describes the use of the dose counting device 10 of the invention with a vial 1 closed by a septum as shown on FIGS. 1A-1C, the dose counting device of the invention could be used in combination with, and mounted on, a medical container free of any septum. For example, the medical container may be a bottle, an ampoule, a flask or any other container usable in the medical field as long as it is provided with an opening for access to the product it contains, regardless of the fact that this opening is closed by a septum or not.

With reference to FIG. 2, the dose counting device 10 comprises a gripping member 20 intended to secure it onto the vial 1, a counting ring 30 intended to provide information on the number of doses of product already withdrawn from the vial 1 and/or still left in the vial 1, a cap 40, intended to be fixed with the gripping member 20, and a cover 50, intended to prevent or allow access to the opening 3*a* of the vial 1, once the dose counting device 10 is coupled to said vial 1.

With reference to FIG. 2, the gripping member 20 will now be described in detail. The gripping member 20 comprises a U-shaped body 21, having a partially tubular wall 22 showing a height suitable for surrounding the collar 3 of the vial 1 (see FIGS. 5A-C), with two free ends 22*a* corresponding to the ends of the branches of the U, the U-shaped body 21 therefore forming a clipping member. Close to each free end 22*a*, the tubular wall 22 is provided on its outer surface with radial peg 23 (only one being visible on FIG. 2). Each free end 22*a* is further provided with a distal front projection forming a radial rim 24. In an embodiment not shown, the tubular wall does not have any free ends but is a closed annular ring, forming another kind of clipping member with the collar of the vial.

Still with reference to FIG. 2, the counting ring 30 is made of a flat cylinder 31 provided with a plurality of outer radial teeth 32 distributed along its periphery 31*a*. The flat cylinder 31 is further provided with a central hole 33 dimensioned and shaped so as to fit around a distal collar 47 of cap 40 as will be described later in reference to FIG. 3. In the example shown in FIGS. 2-7, the dose counting device 10 is intended to be coupled to a multidose vial 1 filled with ten doses of product. As a consequence, the counting ring 30 is provided with information data corresponding to these ten doses of product to be withdrawn from the vial 1: in this view, the flat cylinder 31 is provided with printed digits 34 indicating the numbers 1 to 10, these digits being regularly distributed along the circumference of the flat cylinder 31.

With reference to FIGS. 2 and 3, the cap 40 will now be described in detail. The cap 40 comprises a transversal wall 41 having a substantially circular shape except for a right angle forming a corner 41*a*. A circular rim 42 extends from the transversal wall 41 in the distal direction. A U-shaped skirt 43 extends from the circular rim 42 in the distal direction, the free ends 43*a* of the U forming an opening 43*b* of the skirt 43. Close to each free end 43*a*, the skirt 43 is provided on its outer surface with a recess 43*c* (only one being visible on FIG. 2). The circular transversal wall 41 is provided with a central hole 44 and with a side hole 45 offset from the central hole 44 in the direction of the opening 43*a* of the U-shaped skirt 43. As will appear from the description below, the central hole 44 is intended to face the opening 3*a* of the vial 1 when the dose counting device 10 is coupled to the vial 1. The transversal wall 41 is further provided in its corner 41*b* with a corner hole 46. In an embodiment not shown, the skirt is a closed circular skirt extending from the circular rim 42 in the distal direction, and has no opening.

With reference to FIG. 3, the distal face of the transversal wall 41 is provided with a distal collar 47 extending from the edge of the central hole 44, and provided with a distal outer rim 47*a*. Still with reference to FIG. 3, the U-shaped skirt 43 is provided on its inner wall with a corner transversal rim 48 facing corner hole 46. The corner transversal rim 48 is provided with a central hole 48*a*.

The cap 40 is sized and shaped for receiving therein the counting ring 30 and the gripping member 20: as shown on FIGS. 2 and 5A, the counting ring 30 is imprisoned inside the circular rim 42 and the U-shaped skirt 43 is aligned on the U-shaped element 21 of the gripping member 20 when the dose counting device 10 is in use. In an embodiment not shown, where the shirt has a circular shape, the skirt is aligned on an annular body of the gripping member.

With reference to FIGS. 2 and 4, the cover 50 will now be described in detail. The cover 50 comprises a sheet 51 having substantially the shape of the transversal wall 41 of the cap 40, with a corner 51*b* intended to face the corner 41*b* of the transversal wall 41. The sheet 51 is provided on its proximal face with a printed arrow 52 indicating the counter clockwise rotation of the sheet 51 with respect to a vertical axis 53 located at the corner 51*b*. In addition, on the example shown, a large planar section 51*a* is defined on the proximal face of sheet 51, in order to have space to write information thereon or stick a label. The sheet 51 is provided with a side hole 55 intended to face side hole 45 of the transversal wall 41 of the cap 40, when the dose counting device 10 is in use. With reference to FIG. 4, the distal face of the sheet 51 is provided at its corner 51*b* with a shaft 56 extending in the distal direction and aligned on vertical axis 53, said shaft 56 being terminated by a distal outer rim 56*a*. Proximally spaced from its distal outer rim 56*a*, the shaft 56 is provided with a semi-gear wheel 57, in other words a gear wheel provided with outer radial teeth only on half (180°) or less of its circumference, said radial teeth facing the outside of the sheet 51, as shown on FIG. 4.

The sheet 51 may be made of any material such as as high-density polyethylene, polypropylene, polyvinyl chloride, acrylonitrile-butadiene-styrene (ABS), silicon resin or any other rigid polymer. Alternatively, materials such as metal, wood or glass may be used.

The use of the dose counting device 10 in connection with a vial of FIGS. 1A-1C will now be explained with reference to FIGS. 2-7. In the use position of the dose counting device 10 of the invention, namely when the dose counting device of the invention is coupled to the vial, the cover 50 may adopt a closed position (FIGS. 5A-C, 7) or an open position (FIGS. 6A-C).

With reference to FIGS. 5A-5C, the dose counting device 10 is shown once coupled to a vial 1 and in the closed position of the cover 50. In addition, on these Figures, the dose counting device 10 of FIGS. 2-4 is further provided with a pierceable elastomeric piece 60 lodged in central hole 44 of the cap 40 and traversing the central hole 33 of the counting ring 30 so as to come in contact with the outer surface 4*a* of the septum 4 of the vial 1. The central hole 44 and the pierceable elastomeric piece therefore face the opening 3*a* of the vial 1.

In the present application, "pierceable" means that the septum and the elastomeric piece may be pierced and traversed by the needle of an injection device such as a syringe, an auto-injector, or a reconstitution device, in order for the needle to access the inside of the vial and withdraw the doses of product.

The pierceable elastomeric piece 60 has globally the shape of a flat cylinder and is dimensioned and shaped so as to be received within central hole 44 of the transversal wall 41 of the cap 40 with friction. The pierceable elastomeric piece 60 is made of a material impermeable to gas and liquid capable of flexing under pressure.

Suitable materials for the pierceable elastomeric piece 30 of the adaptor of the invention include natural rubber, acrylate-butadiene rubber, cis-polybutadiene, chlroro or bromobutyl rubber, chlorinated polyethylene elastomers, polyalkylene oxide polymers, ethylene vinyl acetate, fluorosilicone rubbers, hexafluoropropylene-vinylidene fluoride-tetrafluoroethylene terpolymers, butyl rubbers, polyisobutene, synthetic polyisoprene rubber, silicone rubbers, styrene-butadiene rubbers, tetrafluoroethylene propylene copolymers, thermoplastic-copolyesters, thermo-plastic elastomers, or the like or a combination thereof.

Preferably, the elastomeric piece is self-resealing and it automatically seals the hole produced by the piercing of the needle, automatically and rapidly, for example in less than 0.5 seconds, once the needle is removed from the elastomeric piece. This automatic closure step may occur a high number of times, in particular as many times as necessary for removing the number N doses of product initially present in the multidose vial 1. Suitable materials for self-resealing pierceable elastomeric piece include synthetic polyisoprene, natural rubber, silicone rubber, thermo-plastic elastomers, or the like or a combination thereof.

In the use position of the dose counting device 10 of the invention, as shown on FIGS. 5A-5C, the flat cylinder 31 is snap-fitted on the cap 40, by means of its central hole 33 being engaged on the distal collar 47 of said cap 40, and being blocked in the distal direction by distal outer rim 47*a* of distal collar 47, the flat cylinder 31 being able to rotate with respect to said distal collar 47. In addition, the cap 40 is itself snap-fitted on the gripping member 20, by means of its recesses 43*c* being engaged in radial pegs 23 of the tubular wall 22 of U-shaped element 21 of the gripping member 20. As a consequence, the cap 40, as well as the central hole 44, are fixed with respect to the gripping member 20. In embodiments not shown, the cap 40 and the U-shaped element 21 could be integrate and form one single element, namely the gripping member.

In the use position of the dose counting device 10 of the invention, as shown on FIGS. 5A-5C, the cover 50 is linked to the cap 40 by means of shaft 56 traversing corner hole 46 of the transversal wall 41 and being snap-fitted into corner transversal rim 48 after distal outer rim 56*a* of said shaft 56 has overcome central hole 48*a* of said corner transversal rim 48. The shaft 56 is allowed to rotate within corner hole 46, around axis 53 in counter clockwise rotation direction indicated by arrow 52.

On FIGS. 5A-5C, the dose counting device 10 is coupled to vial 1. In this view, the gripping member 20 has been mounted on the collar 3 of the vial in a sliding way, and the radial rims 24 now surround said collar 3, thereby securing the dose counting device 10 on the vial 1. In this coupled position of the dose counting device 10 on the vial 1, the central hole 44, in which is lodged pierceable elastomeric piece 60, is aligned on the septum 4 and opening 3*a* of the vial 1.

In addition, in the closed position of cover 50, as shown on FIGS. 5A-5C, the central portion of the sheet 51 closes central hole 44, thereby preventing any access to said central hole 44 and to opening 3*a* of the vial 1 by the needle of an injection device. In this position also, the side hole 55 of the sheet 51 faces the side hole 45 of the cap 40 and the user is allowed to see one digit printed on the flat cylinder 31 of the counting ring 30. In the example shown, with reference to FIG. 5B, the digit "10" is visible, meaning for example that no dose has been withdrawn yet from the vial 1 and that ten doses are left therein.

When the user is ready to withdraw a first dose of product, he rotates the cover 50 in the counter clockwise direction so as to cause a 180° rotation of said cover 50, as shown on FIGS. 6A-6C, where the cover 50 is in its open position. As shown on these Figures, in this position of the cover 50, the central portion of the sheet 51 does not cover the central hole 44 of the cap 40 anymore and access to the central hole 44 and to the opening 3*a* of the vial 1 by a needle capable of piercing the pierceable elastomeric piece 60 and the septum 4 is no more prevented. In addition, the rotation of the cover 50 from its closed position to its open position has not caused any movement of the flat cylinder 31, which still displays the figure "10" through side hole 45 of the cap 40 as shown on FIG. 6B. Indeed, during this rotation of the cover 50, the shaft 56 and the semi gear wheel 57 have also completed a 180° rotation: as a consequence, as shown on FIG. 6C, in the open position of the cover, an end tooth of the semi gear wheel 57 becomes engaged with an outer radial tooth 32 of the flat cylinder 31, but has not cooperated yet with the plurality of outer radial teeth 32 of flat cylinder 31 in order to cause the rotation of the counting ring 30.

Once the user has withdrawn the dose of product from the vial 1, he continues the counter clockwise rotation of the cover 50 in order to bring the cover 50 back in its closed position so as to cover again and protect central hole 44 of cap 40. During this second 180° rotation of the cover from its open position to its closed position, the teeth of the semi gear wheel 57 cooperate with the outer radial teeth 32 of the flat cylinder 31 in which they are engaged. The flat cylinder 31 is therefore caused to rotate and the following digit of the flat cylinder 31, namely digit "9" is now displayed through side holes 45 and 55 as shown on FIG. 7.

In the embodiment shown on FIGS. 2-7, the shaft 56 and the semi gear wheel 57 together with the outer radial teeth 32 of the flat cylinder 31 form an incrementing system for automatically rotating the counting ring 30 on a determined angle each time the user moves the cover from its open position to its closed position. The rotation of the counting ring and the change of digit displayed in holes 45 and 55 are therefore dependent on a two-step process, namely moving the cover 50 from its closed position to its open position in a first step, and moving the cover 50 from its open position to its closed position in a second step, the rotation of the counting ring taking place only during the second step. This system therefore tolerates incomplete or accidental manipulation of the cover 50 without impeding the reliability of the digit that indicates the number of remaining doses and which is displayed to the user. Indeed, since the counting ring 30 only rotates during the second step, if the user, accidentally or not, only partially performs the first step, then the rotation of the counting ring 30 will not take place and the digit indicating the number of remaining doses will not change. In addition, the position of the cover 50 with respect to the digit may be tailored by varying the number of teeth of the semi-gear wheel 57. For example, the digit may be changed only when masked by the cover 50 during the second step, i.e. when not visible by the user, so that the user is not disturbed by this changing, the new digit being further clearly visible by the user through holes 45 and 55 once the second step is over. The user is therefore provided with accurate information on how many doses of product are left in the vial and all risk of confusion is eliminated.

Furthermore, with such an incrementing system, the dose counting device has a very compact size. This small size is particularly valuable as multidose vials are usually stored in cold places, such as medical refrigerator or medical cold box having limited space capacity. Furthermore, the dose counting device of the invention is easy to handle even with a single hand as the rotation of the cover can be easily realized.

With reference to FIGS. 8-11, is shown a dose counting device 110 in accordance with a second embodiment of the invention, in which no incrementing system is present, and in which the user may rotate the counting ring manually. The reference signs designating the same elements as in embodiment of FIGS. 2-7 have been maintained.

With reference to FIG. 10, the cap 140 comprises a transversal wall 141 from which extends a skirt 143 in the distal direction. The transversal wall 141 is provided with a central hole 144. The cap 140 is provided with a window 142 allowing the flat cylinder 31 of the counting ring 30 (see FIGS. 8 and 9) to be reached by the hand of the user. At its corner 141*b*, the proximal face of the transversal wall 141 is provided with a shaft 146 extending in the proximal direction.

With reference to FIG. 11, the cover 150 comprises a sheet 151 provided with a corner hole 156 at its corner 151*b*.

On FIG. 8, the dose counting device 110 is shown coupled to the vial 1 with the cover 150 in the closed position. The cover 150 is linked to the cap 140 by means of shaft 146 being lodged within corner hole 156. When the user is ready to withdraw a dose of product from the vial 1, he rotates the cover 150 in the clockwise direction around the axis of shaft 146 and causes said cover 150 to complete a 180° rotation, as shown on FIG. 9. In this open position of the cover, access to the central hole 144 and to the pierceable elastomeric piece 60, to the septum and to the opening 3*a* of the vial 1 is not prevented anymore and the user may withdraw a dose of product from the vial 1.

Once the dose of product is withdrawn, the user continues the clockwise rotation of the cover 150 in order to bring the cover 150 back to its closed position. During this second 180° rotation of the cover 150 from its open position to its closed position, no cooperation occurred between the flat cylinder 31 and any part of the cover 150. As a consequence, the user must manually rotate the flat cylinder 31 so as to display the number of doses left in the vial 1: the user is able to complete this step as he may reach the flat cylinder 31 through window 142, as shown on FIGS. 8 and 9.

With reference to FIGS. 12-17 is shown a dose counting device 210 in accordance with a third embodiment of the invention, in which the cover is movable in translation with respect to the gripping member.

The dose counting device 210 is intended to be coupled on a multidose vial 1 as shown on FIGS. 1A-1C. As mentioned before, although the following description describes the use of the dose counting device 210 of the invention with a vial 1 closed by a septum as shown on FIGS. 1A-1C, the dose counting device of the invention could be used in combination with, and mounted on, a medical container free of any septum. For example, the medical container may be a bottle, an ampoule, a flask or any other container usable in the medical field as long as it is provided with an opening for accessing the product it contains, regardless of the fact that this opening is closed by a septum or not.

Like previous embodiments, the dose counting device 210 comprises a gripping member 220 intended to secure it onto the vial 1, a counting ring 230 intended to provide information on the number of doses of product already withdrawn from the vial 1 and/or still left in the vial 1, a cap 240, intended to be fixed with the gripping member 220, and a cover 250, intended to prevent or allow access to the opening 3*a* of the vial 1, once the dose counting device 210 is coupled to said vial 1.

With reference to FIG. 12, the gripping member 220 comprises a U-shaped body 221, having a partially tubular wall 222 showing a height suitable for surrounding the collar 3 of the vial 1, with two free ends 222*a* corresponding to the ends of the branches of the U, the U-shaped body 221 therefore forming a clipping member. Close to each free end 222*a*, the tubular wall 222 is provided on its outer surface with radial peg 223 (only one being visible on FIG. 12). Each free end 222*a* is further provided with a distal front projection forming a radial rim 224. In an embodiment not shown, the tubular wall does not have any free ends but is a closed annular ring, forming another kind of clipping member with a collar of a vial.

Still with reference to FIG. 12, the counting ring 230 is made of a flat cylinder 231 provided with a plurality of outer radial projections 232 distributed along its periphery 231*a*. Each radial projection 232 is provided with a sloped surface 232*a* and with a radial surface 232*b*. The flat cylinder 231 is further provided with a central hole 233 dimensioned and shaped so as to fit around a distal collar 247 (see FIG. 13) of cap 240 in the same manner as that described for embodiment of FIGS. 2-7. Like in previous embodiments, the dose counting device 210 is intended to be coupled to a multidose vial 1 filled with ten doses of product. As a consequence, the counting ring 230 is provided with information data corresponding to these ten doses of product to be withdrawn from the vial 1 like in previous embodiments.

With reference to FIGS. 12 and 13, the cap 240 will now be described in detail. The cap 240 comprises a transversal wall 241 having a substantially rectangular shape. A rim 242 extends from the transversal wall 241 in the distal direction. A U-shaped skirt 243 extends from the rim 242 in the distal direction, the free ends 243*a* of the U forming an opening 243*b* of the skirt 243. Close to each free end 243*a*, the skirt 243 is provided on its outer surface with a recess 243*c* and with an outer peg 249. The transversal wall 241 is provided with a central hole 244 and with a side hole 245 offset from the central hole 244 in the direction of the opening 243*a* of the U-shaped skirt 243. As will appear from the description below, the central hole 244 is intended to face the opening 3*a* of the vial 1 when the dose counting device 210 is coupled to the vial 1. In an embodiment not shown, the skirt is a closed circular skirt extending from the circular rim 42 in the distal direction, and has no opening.

With reference to FIG. 13, the distal face of the transversal wall 241 is provided with a distal collar 247 extending from the edge of the central hole 244, and provided with a distal outer rim 247*a*. Still with reference to FIG. 3, the inner wall of cap 240 is provided with an oblique leg 248 extending towards the center of the cap 240.

The cap 240 is sized and shaped for receiving therein the counting ring 230 and the gripping member 220: as shown on FIGS. 12 and 15C, the counting ring 230 is imprisoned inside the circular rim 242 and the U-shaped skirt 243 is aligned on the U-shaped element 221 of the gripping member 220 when the dose counting device 210 is in use.

With reference to FIGS. 12 and 14, the cover 250 will now be described in detail. The cover 250 comprises a sheet 251 having substantially the shape of the transversal wall 241 of the cap 240. The proximal face of the sheet 251 is provided with a large flat surface 251*a* in order to provide an area to write information thereon or stick a label. The sheet 251 is further provided with a distal skirt 252 capable of receiving the cap 240: as will appear from the following description, the cap 240 is movable in translation with respect to the cover 250 along the direction of the free ends of the U of the U-shaped skirt 243. The sheet 251 is provided with a side hole 255 intended to face side hole 245 of the transversal wall 241 of the cap 240, when the dose counting device 210 is in use. With reference to FIG. 14, the inner wall of the distal skirt 252 of the cover 250 is provided with a flexible leg 253 capable of deflecting from a rest position, in which it extends towards the center of the cover 250 to a stressed position, in which it is aligned with the wall of the distal skirt 252 and in which it is lodged into a transversal window 254 of said wall (see FIG. 12).

The lateral walls of the distal skirt 252 are further provided with a transversal window 256 distally spaced from transversal window 254.

The use of the dose counting device 210 will now be explained with reference to FIGS. 12-17. For sake of clarity, the vial 1 is not shown on these figures, but it is meant that the dose counting device 210 is coupled on a vial as shown on FIGS. 1A-1C, via its gripping member 220, in the same manner as described for previous embodiments, and that the central hole 244 faces the opening 3*a* of the vial 1.

In the use position of the dose counting device 210 of the invention, the flat cylinder 231 is snap-fitted on the cap 240, by means of its central hole 233 being engaged on the distal collar 247 of said cap 240, and being blocked in the distal direction by distal outer rim 247*a* of distal collar 247, the flat cylinder 231 being able to rotate with respect to said distal collar 247. In addition, the cap 240 is itself snap-fitted on the gripping member 220, by means of its recesses 243*c* being engaged in radial pegs 223 of the tubular wall 222 of U-shaped element 221 of the gripping member 220. As a consequence, the cap 240, as well as the central hole 244, is fixed with respect to the gripping member 220. In embodiments not shown, the cap 240 and the U-shaped element 221 could be integrated and could form one single element, namely the gripping member.

In the use position of the dose counting device 210 of the invention, as shown on FIGS. 15A-15C, the cover 250 is linked to the cap 240 by means of the outer pegs 249 of cap 240 being received in translation into the distal transversal window 256 of cover 250. With reference to FIG. 15C, the oblique leg 248 of cap 240 is in abutment against a radial surface 232*b* of one projection 232 of the flat cylinder 231, thereby preventing the flat cylinder 231 to rotate in the counter clockwise direction with respect to this FIG. 15C. In addition, the flexible leg 253 is in its rest position and is in abutment against a sloped surface 232*a* of another projection 232 of the flat cylinder 231.

In the closed position of cover 250, as shown on FIGS. 15A-15C, the central portion of the sheet 251 closes central hole 244, thereby preventing any access to said central hole 244 and so to the opening of the vial by the needle of an injection device. In this position also, the side hole 255 of the sheet 251 faces the side hole 245 of the cap 240 and the user is allowed to see one digit printed on the flat cylinder 231 of the counting ring 230. In the example shown, with reference to FIG. 15A, the digit "10" is visible, meaning for example that no dose has been withdrawn yet from the vial and that ten doses are left therein.

When the user is ready to withdraw a first dose of product, he pushes the cover 250 in the direction of the arrow F1 shown on FIG. 15C, so as to move it to its open position, as shown on FIGS. 16A-16C. As shown on these Figures, in this position of the cover 250, the side hole 255 of the sheet 251 comes in regards to the central hole 244 of the cap 240 and access to the central hole 244 and to the opening of the vial by a needle is no more prevented. In addition, the translation of the cover 250 from its closed position to its open position has not caused any movement of the flat cylinder 231, which still displays the figure "10" through side hole 245 of the cap 240 as shown on FIG. 16A. Indeed, during this translation of the cover 250, the flexible leg 253 has been caused to deflect inside the transversal window 254 by adjacent projection 232 of the flat cylinder 231, said flat cylinder 231 being prevented from rotating in the counter clockwise direction with respect to FIG. 16C, by means of the oblique leg 248 being in abutment against a radial surface 232*b* of one projection 232. Once the cover 250 has reached it open position as shown on FIGS. 16A-C, the flexible leg 253 has escaped adjacent projection 232 and has come back to its rest position, as shown on FIG. 16C.

Once the user has withdrawn the dose of product from the vial, he pushes back the cover 250 in the direction of the arrow F2 shown on FIG. 16C order to bring the cover 250 back in its closed position so as to cover again and protect central hole 244 of cap 240. During this return translation of the cover 250 from its open position to its closed position, the free end of the flexible leg 253 comes in abutment against the radial surface of adjacent projection 232, and pushes on said radial surface 232*b*. The flat cylinder 231 is therefore caused to rotate in the clockwise direction with respect to FIG. 16C, and the following digit of the flat cylinder 231, namely digit "9" is now displayed through side holes 245 and 255 as shown on FIG. 17. The translation movement of the cover 250 is easy to realize and the user can open and close the cover 250 of the dose counting device 210 with a single hand.

In another embodiment (not shown), the dose counting device 210 is provided with biasing means, such as a spring, forcing the cover 250 in its closed position. This spring ensures that the dose counting device is not left in the open position of the cover for an extended period of time and therefore reduces the risk of contamination of the pierceable elastomeric piece and/or the septum.

In the embodiment shown on FIGS. 12-17, the flexible leg 253, the oblique leg 248 together with the projections 322 of the flat cylinder 231 form an incrementing system for automatically rotating the counting ring 230 on a determined angle each time the user moves the cover from its open position to its closed position. As seen above, the rotation of the counting ring and the change of digit displayed in holes 245 and 255 are therefore dependent on a two-step process, namely moving the cover 250 from its closed position to its open position in a first step, and moving the cover 250 from its open position to its closed position in a second step, the rotation of the counting ring taking place only during the second step. This system therefore tolerates incomplete or accidental manipulation of the cover 250 without impeding the reliability of the digit that indicates the number of remaining doses and which is displayed to the user. Indeed, since the counting ring 230 rotates only during the second step, if the user, accidentally or not, only partially performs the first step, the rotation of the counting ring 230 will not take place and the digit indicating the number of remaining doses will not change. The user is therefore provided with accurate information on how many doses of product are left in the vial and all risk of confusion is eliminated.

In other embodiments not shown, the flexible leg may be capable of engaging a radial surface of the periphery of the counting ring when the cover moves from its closed position to its open position, thereby causing rotation of the counting ring. As an example, this embodiment could be useful to indicate to the user how many times the cover has been opened.

The dose counting device and assembly of the invention allow piercing the septum of a multidose vial yielding favorable hygienic and aseptic conditions multiple successive times while providing the user with accurate information on how many doses of product are left in the vial, as the counting ring may be automatically incremented each time a user moves the cover from its closed position to its open position, and then back to its closed position.

Additionally, in all the previous described embodiments of the dose counting device of the present invention, the dose counting device may be provided with a time monitoring system (not shown). Indeed, the content of the vial may be considered as contaminated after a limited period of time, for example until 28 to 30 days. Therefore, a time monitoring system may be added to the dose counting device according to the invention in order to monitor the elapsing time from the first dose withdrawing or to indicate to the user what is the time remaining before the 28 or 30 days deadline.

This time monitoring system may be an electronic timer or a system based on the diffusion of ink into a circuit. For example, the elapsing or remaining time can be monitored by the kinetic of ink progression in a microfluidic circuit. Such systems are particularly attractive because they are small and reliable. For example, such a system could be integrated onto the large central planar section 51*a* of the dose counting device 10 or onto the large flat surface 251*a* of the dose counting device 210. Some time monitoring systems are commercially available under the trademark Timestrip®.

Furthermore, the time monitoring system could be triggered either manually by the user or automatically. An automatic trigger could occur when the dose counting device is mounted on the collar 3 of the vial 1 which assumes a first dose withdrawing shortly afterwards. For example, such time monitoring system could be under the form of a label, sticked onto the dose counting device (10; 210) and could be triggered by an additional peg (not shown) placed into a blister intended to come in contact with the time monitoring system and therefore activate it when the user applies a distal pressure on said blister.

Such a system could prevent the injection of potentially expired vaccines or drugs to patients, but could also facilitate the supply chain or stock management in drugstores or even avoid wastage of valuable drugs and vaccines by encouraging the use of the first opened vials.

The user may repeat the piercing step with the needle of a new empty syringe until all the doses contained in the vial are removed. The dose counting device of the invention acts as a protection of the septum of the vial during the lifetime of the vial.

When present, the pierceable elastomeric piece and the septum of the medical container are in contact, for example in tight contact, once the dose counting device is secured onto the medical container. In embodiments where both the pierceable elastomeric piece and the septum of the medical container are self-resealing, no possibility of communication exist between the inside of the medical container and the outside environment at the time the needle of the injection device is removed from both the septum and the pierceable elastomeric piece, after withdrawal of a dose of product from the medical container. This therefore restricts or prevents the product contained in the medical container from being contaminated by outside contaminants such as bacteria, unpurified water, particles, viruses, etc. . . . The dose counting device of the invention thus allows a hermetic sealing of the contents of the medical container it is secured on, even during the removal of the needle. The inside of the medical container is kept in aseptic conditions before, during and after a withdrawal of a dose from the medical container.

This dose counting device of the invention is very easy to use as it can be used with a single hand. Additionally, the dose counting device of the invention is very reliable as no battery neither electronic system are used avoiding any disturbance within time.

Furthermore, during an immunization campaign, with the dose counting device of the invention, the number of injected doses can be quickly compared to the number of expected patients, thus ensuring that each patient received a dose of vaccine. Finally, the stock management is facilitated for drugstores and the supply chain can be optimized to reduce medicine wastage.

The invention claimed is:

1. A dose counting device having a central longitudinal axis for coupling with a medical container filled with a number N of doses of a product to be withdrawn therefrom, said medical container being provided with an opening for access to said product, the dose counting device comprising—:

a gripping member for securing the dose counting device to the medical container, said gripping member defining a hole wherein, with the dose counting device coupled to the medical container, the hole is longitudinally aligned with the opening, a counting ring rotatably mounted with respect to said gripping member, said counting ring being provided with information data corresponding to the number N of doses, a cover movable between a closed position, in which said cover prevents access to said hole, and an open position, in which the cover does not prevent access to said hole wherein at least a portion of the cover moves radially outward with respect to the central longitudinal axis when the cover is transitioned from the closed position to the open position.

2. The dose counting device of claim 1, further comprising an incrementing system coupled to said cover and to said counting ring, said incrementing system adapted to automatically rotate the counting ring a predetermined angle about the longitudinal axis upon the cover moving from the open position to the closed position.

3. The dose counting device of claim 2, wherein said incrementing system comprises an active surface and said counting ring comprises a complementary active surface, said active surface adapted to engage the complementary active surface to rotate the counting ring when the cover moves from the open position to the closed position.

4. The dose counting device of claim 3, wherein said cover is movable in rotation around an axis with respect to said gripping member when said cover moves from the closed position to the open position and vice-versa, said incrementing system comprises a part of a gear wheel located on said cover, said gear wheel being rotatable around the axis and being provided with a plurality of radial teeth capable of cooperating with a plurality of complementary radial teeth provided on the periphery of the counting ring, when said cover moves back from the open position to the closed position.

5. The dose counting device of claim 3, wherein said cover is movable in translation with respect to said gripping member, when said cover moves from the closed position to the open position and vice-versa, said incrementing system comprises a flexible leg located on said cover, said flexible leg adapted to escape a sloped surface of the periphery of said counting ring when said cover moves from the closed position to the open position, said flexible leg adapted to engage a radial surface of said periphery of said counting ring when said cover moves back from the open position to the closed position.

6. The dose counting device of claim 1, further comprising a pierceable elastomeric piece fixed with respect to the gripping member, wherein, with the dose counting device coupled to the medical container, the pierceable elastomeric piece faces the opening of the medical container.

7. The dose counting device of claim 1, further comprising a biasing means for forcing the cover in the closed position.

8. Assembly comprising a medical container comprising an opening and filled with a number N of doses of a product to be withdrawn therefrom via said opening and a dose counting device according to claim 1.

9. The assembly of claim 8, wherein said opening is closed by a septum.

10. The assembly of claim 9, further comprising a pierceable elastomeric piece fixed with respect to the gripping member, wherein, with said dose counting device coupled to said medical container, said pierceable elastomeric piece is in contact with said septum.

11. The assembly of claim 8, wherein, said opening is a collar closed by a septum, said gripping member comprises a clip adapted to surround said collar.

12. The assembly of claim 1, wherein the radial movement of the cover comprises translational movement.

13. The assembly of claim 12, wherein the translational movement of the cover comprises rectilinear movement.

14. The assembly of claim 1, wherein the radial movement of the cover comprises rotational movement about a pivot axis spaced a distance apart from the central longitudinal axis.

15. A dose counting device having a longitudinal axis for coupling with a medical container filled with a number N of doses of a product to be withdrawn therefrom, said medical container being provided with an opening for access to said product, the dose counting device comprising:

a gripping member for securing the dose counting device to the medical container, said gripping member defining a hole wherein, with the dose counting device coupled to the medical container, the hole is longitudinally aligned with the opening, a counting ring rotatably mounted with respect to said gripping member, said counting ring being provided with information data corresponding to the number N of doses, a cover movable with respect to said hole between a closed position, in which said cover prevents access to said hole, and an open position, in which the cover does not prevent access to said hole, and an incrementing system coupled to said cover and to said counting ring, said incrementing system adapted to automatically rotate the counting ring a predetermined angle about the longitudinal axis only upon the cover moving from the open position to the closed position.

* * * * *